United States Patent [19]

Klemm

[11] Patent Number: Plant 7,494

[45] Date of Patent: Apr. 9, 1991

[54] GERANIUM PLANT NAMED BRENESO

[75] Inventor: Siegfried Klemm, Stuttgart, Fed. Rep. of Germany

[73] Assignee: Klemm & Sohn, Fed. Rep. of Germany

[21] Appl. No.: 356,127

[22] Filed: May 24, 1989

[51] Int. Cl.[5] ..... A01H 5/00

[52] U.S. Cl. ..... Plt./68

[58] Field of Search ..... Plt./68

*Primary Examiner*—Howard J. Locker

*Attorney, Agent, or Firm*—Charles W. Rummler

[57] ABSTRACT

A new low growing Geranium cultivar particularly distinguished by its profuse and continuous production of relatively large flower clusters of about 10 cm. in diameter and comprised of large florets of a roseine purple color and having a diameter of about 5.2 cm., the flower clusters being carried on stalks that are only about 13 to 14 cm. long extending through foliage having relatively small leaves of medium to light green color and without zoning. Thus this plant provides a compact growing novelty geranium that always looks fresh. In September the plant reaches a height of about 23 cm., exclusive of the flowers, and is thus well fitted for bedding, or balcony and container adaption. The color is also new in the geranium market.

1 Drawing Sheet

BACKGROUND OF THE NEW PLANT

My new geranium is a seedling of unknown parentage which was part of a seed collection of wildly pollenated plants which flowered for the first time in 1984 and this plant having been noticed by me because of its new color. Since my discovery of this plant, it has been propagated vegetatively through a series of generations and under controlled conditions for four years thereby demonstrating that its novel characteristics are fixed and that its homogeneity can be assured.

DESCRIPTION OF THE DRAWING

This new and compact growing plant is illustrated by the accompanying full-color photographic drawing which illustrates the growth nature of this new plant and the character of its flower clusters and buds, the color rendition being as nearly true to that herein specified as is reasonably possible to obtain by conventional photographic procedures.

DESCRIPTION OF THE NEW PLANT

The following is a detailed description of my new variety of Geranium plant as observed at Stuttgart, West Germany in 1988 with the color designations according to The R.H.S. Color Chart published by The Royal Horticultural Society of London, England.

THE PLANT

Origin: Seedling.
Parentage: Unknown.
Classification:
- *Botanic.*—*Pelargonium zonale* hybrid.
- *Commercial.*—Geranium.

Form: Bush.
Shape: Compact.
Height: Up to about 23 cm. without flower, by September.
Growth habit: Medium to low with good strength.
Branching character: Normal.
Flower stem:
- *Length.*—About 13 to 14 cm.

Foliage:

- *Quantity.*—Normal.
- *Leaf size.*—Small with bicrenate margin.
- *Texture.*—Smooth.
- *Color.*—Upper side — Medium Green without zonation. Underside — Lighter Green.

THE BUD

Size: Normal.
- *Diameter.*—About 10 to 11 mm.
- *Length.*—About 15 mm.

Shape: Ovoid with acuminate apex.
Rate of opening: Medium.
Color of floret petals:
- *When sepals first divide.*—Light pink R.H.S. 68-C.
- *When petals begin to unfurl.*—Pink R.H.S. 68-A.

Sepals:
- *Number.*—Five.
- *Shape.*—Elongate with acute apex.
- *Character.*—The sepals stand up when the florets open.
- *Color.*—Both inside and outside — Green.

Calyx:
- *Shape.*—Cup-shaped.
- *Size.*—Broad.
- *Splitting.*—Calyx does not split.
- *Aspect.*—Very little of hairs.

Stalk of flower clusters:
- *Length.*—About 13 to 14 cm.
- *Character.*—Erect, rigid and strong.
- *Color.*—Green.

THE INFLORESCENCE

Blooming habit: Continuous and profusely from early Spring to Fall.
Size of flower cluster: Large.
- *Diameter.*—About 10 cm.

Florets:
- *Size.*—Very large. Diameter — About 5.2 cm. Depth — About 1.5 cm.

Borne: Singly on a stem of the umbel formed cluster.
Shape:
- When bloom first open.—Cup-shaped.
- When bloom matures.—Flat.

Petalage:

*Number of petals.*—10.

*Arrangement.*—Imbricated.

*Form.*—Generally reniform with entire margins.

*Texture.*—Soft.

*Aspect.*—Satiny.

*Color.*—All petals: Body — Pink roseine purple, R.H.S. 68-A.

Persistence: The flower petals dry and drop off.

Lasting quality: About 15 days.

THE REPRODUCTIVE ORGANS

Stamens:

*Number.*—Seven.

*Arrangement.*—Around the pistil.

*Anthers.*—Size: About 1.5 cm. Color: Dark orange.

*Filaments.*—Length: About 4 mm. Color: Light green.

*Pollen.*—Color: Orange.

Pistils:

*Number.*—One.

*Style.*—Length: About 5 mm. Color: Light green.

*Stigma.*—Nature: Five-lobed.

Color: Red.

Character of the ovaries: Normal.

THE FRUIT

Fertility: The fruit is fertile.

Shape: Ovoid.

Color: Dark brown at maturity.

This new geranium is a compact growing novelty plant with a very attractive inflorescense coloration, very large flower clusters with relatively short stalks and altogether the plant has a low growth habit making it well fitted as a potted plant.

I claim:

1. The new and distinctive Geranium cultivar substantially as herein shown and described, particularly distinguished by its low growth habit and the very large size of its roseine purple florets mostly grouped to provide very large umbel formed clusters.

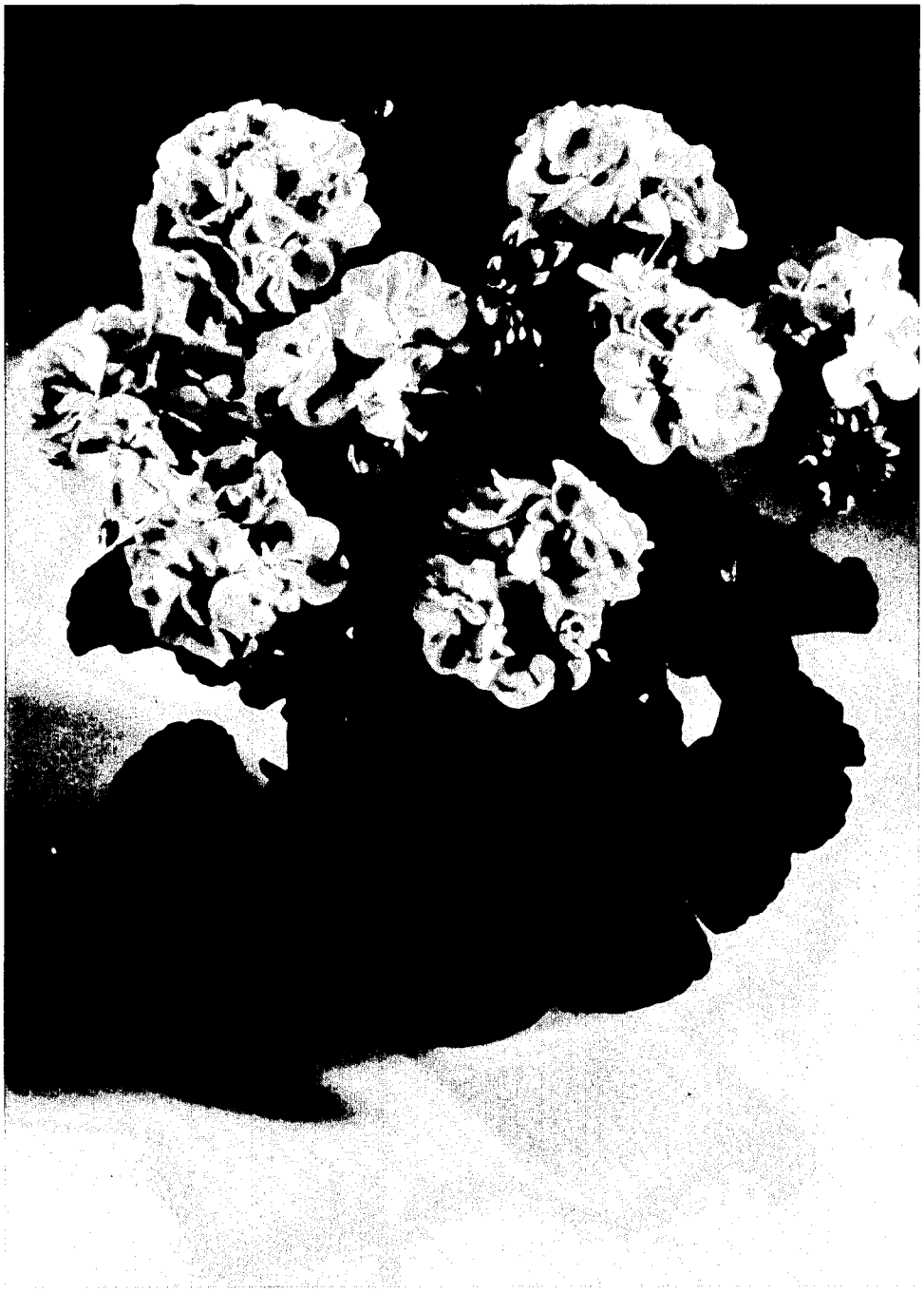

* * * * *